United States Patent [19]

Yoshizawa

[11] Patent Number: 4,792,227

[45] Date of Patent: Dec. 20, 1988

[54] APPARATUS FOR MEASURING THE REFRACTIVE INDEX OF A SUBSTRATE FOR AN OPTICAL RECORDING MEDIUM AND METHOD OF MEASURING THE SAME

[75] Inventor: Akihiko Yoshizawa, Hachioji, Japan

[73] Assignee: Olympus Optical Co., Ltd., Tokyo, Japan

[21] Appl. No.: 21,286

[22] Filed: Mar. 3, 1987

[30] Foreign Application Priority Data

Mar. 3, 1986 [JP] Japan ................................. 61-45931

[51] Int. Cl.$^4$ ..................... G01N 21/21; G01N 21/41
[52] U.S. Cl. ..................................... 356/128; 356/367
[58] Field of Search ............... 356/128, 364, 365, 366, 356/367, 368, 369, 370; 351/128, 364–370

[56] References Cited

U.S. PATENT DOCUMENTS 3,724,952 4/1973 Vossberg ............................. 356/368
4,053,232 10/1977 Dill et al. ............................ 356/369

FOREIGN PATENT DOCUMENTS 241120 11/1986 Fed. Rep. of Germany ...... 356/376

OTHER PUBLICATIONS

McCrackin et al. "Measurement of the Thickness and Refractive Index of Very Thin Films and the Optical Properties of Surfaces by Ellipsometry", Journal of Research of the National Bureau of Standards, vol. 67A, No. 4, (Jul.–Aug. 1963).

Primary Examiner—R. A. Rosenberger
Attorney, Agent, or Firm—Armstrong, Nikaido, Marmelstein & Kubovcik

[57] ABSTRACT

An apparatus (31) and method for measuring the refractive index of an optical recording medium substrate (34) wherein an angle of incidence of a polarized beam (33) is set at an oblique angle of incidence with the substrate (34), the polarized direction of the polarized beam (33) is varied for the substrate (34) in this state, the transmitted or reflected light beam by the substrate is received by a light receiving means (36) through a light analyzer means (35) in the crossed Nichol state and the received light amount for the polarized angle is measured and is compared with a theoretical formula so that the refractive index in the thickness direction of the substrate can be measured.

5 Claims, 9 Drawing Sheets

APPARATUS FOR MEASURING THE REFRACTIVE INDEX OF A SUBSTRATE FOR AN OPTICAL RECORDING MEDIUM AND METHOD OF MEASURING THE SAME

FIELD OF THE INVENTION

This invention relates to an apparatus and method for measuring the refractive index in the thickness direction of an optical information recording medium substrate used to record, reproduce or erase information by radiating a light beam with an optical pickup.

BACKGROUND OF THE INVENTION

Recently, there has come to be noted an optical information recording and reproducing apparatus whereby information can be recorded at a high density in an optical recording medium by collecting light beams and projecting them onto this recording medium and the recorded information written into the recording medium can be read out (reproduced) at a high speed by receiving with a light detector the light returning from this recording medium.

The above mentioned recording medium may be a photomagnetic disc wherein, on a substrate such as acrylate resin as PMMA, there is formed a magnetic recording layer on which the light beams having passed through this substrate are collected and projected and the polarized plane of the returning light rotates in response to the magnetized direction of the part forming a recording film or recording layer different in the returning light amount.

As disclosed in Japanese Patent Laid Open No. 74701/1982, the above mentioned acrylate resin is high in the optical characteristics but has a defect in that the hygroscopicity is so high as to deflect the recording medium surface.

Therefore, it is considered to be effective to use for the substrate a polycarbonate (abbreviated as PC hereinafter) resin or the like which is hard to deflect, high in form stability and high in mechanical strength.

In case the above mentioned PC resin or the like is to be used for the substrate, it will be necessary to well match its optical characteristics. For example, in case its refractive index is large, the optical distance per unit length will become so long that the thickness of the substrate will not be able to be made large. Therefore, it is necessary to investigate the refractive index of the material to be used for the substrate and, as the refractive index varies depending on the method of molding the substrate in some cases, it is desirable to measure the refractive index on the substrate form made by using an actual molding method.

FIG. 1 shows an apparatus 1 for measuring the double refractive index of a disc-shaped recording medium substrate which is a prior art example.

That is to say, a random polarized laser beam of an He-Ne laser 2 has its transmitted light beam made a predetermined linear polarized light beam by a polarizer 3 such as a Glan-Thompson prism (abbreviated as GTP) and is then projected onto a substrate 4 as a measured medium. The light bundle having passed through this substrate 4 passes through a phase compensating plate 5 of Babinet-Soleil arranged so as to be opposed to the above mentioned polarizer 3, then passes through a light analyzer 6 such as a GTP set in a light erasing position (crossed Nichol) so as to pass the polarized light intersecting at right angles with the above mentioned polarizer 3 and is received by a light receiving element 17. In the case of the polarized beam made incident upon the above mentioned substrate 4, if the substrate 4 is of a uniaxial (crystal) characteristic in which the optical axis becomes vertical to the substrate plane, even if the polarized direction is varied by rotating the polarizer 3, no phase difference (becoming elliptic) will be produced in the substrate 4. However, when the optical axis is in the substrate plane, a phase difference will be produced in response to the angle made by the polarized direction and the optical axis and, even in the case of a biaxial (crystal) characteristic, a phase difference will be produced in the substrate 4 by changing the polarized direction of the polarized beam. Therefore, if the phase difference produced in this substrate 4 is erased by moving in the vertical direction (in the paper plane) two wedges, for example, the right optical rotation plate 5b, among the left optical rotation plate 5a and right optical rotation plate 5b, in the phase compensating plate 5, and uniformly varying the thickness of the two plates, the light passing through the light analyzer 6 in the crossed Nichol state will be erased for the polarizer 3 and the signal output from the light receiving element 7 will become a minimum. The double refractive index in the plane of the substrate 4 can be measured from the displacement of the above mentioned phase compensating plate 5.

The refractive index in the thickness direction of the substrate 4 is not known at all in the measuring method of the above mentioned prior art. Therefore, this method is insufficient to be used for the substrate of an optical recording medium. That is to say, in the case of being projected onto the recording layer through the substrate of the recording medium, parallel light bundles are focused to be in the form of a spot and this light collecting angle or the number of apertures N.A. is considerably large. In the position of the substrate surface, the light bundles are kept defocused so as to be hard to be influenced by dust or the like. When the light bundles are thus collected, in case the substrate is of an optical material showing a double refractive index, the refractive index component in the thickness direction will influence the light bundles passing through the substrate. This fact shall be explained in the following.

In case an injection-molded PC plate is used for the above mentioned substrate, this substrate will show double refraction as in a uniaxial crystal and will have an optical axis in the direction vertical to the substrate plane in most cases. The refractive index (no) for ordinary light and refractive index (ne) for extraordinary light are different from each other.

Therefore, a linear polarized light incident upon this substrate as inclined with respect to the optical axis (in the direction vertical to the substrate plane) will produce a phase difference due to the double refraction when the angle formed by the polarizing direction and the plane of incidence is other than a specific angle and will produce an ellipse (the linear polarized light will become an elliptic polarized light).

The reason why such an ellipse is produced shall be explained in the following with reference to FIGS. 2 and 3.

FIG. 2 is an explanatory view showing how a laser beam 14 is pressed into a part of a substrate 12, forming a disc 11 of an objective, to irradiate it in the form of a spot. In the drawing, only a part of the disc 11 is shown.

The laser beam 14 is a linearly polarized light in which the polarized direction is a linearly polarized light intersecting at right angles with the radial direction 16 of the substrate 12 as shown by the reference numeral 15 and includes a beam portion (S polarized light) 21 incident as intersected at right angles with the polarized direction and a beam portion (P polarized light) 22 incident parallelly with the polarized direction, for example, beam portions 23 and 24 incident as inclined by 45 degrees respectively with respect to these beam portions. These beam portions 23 and 24 become polarized light including both components of the S polarized light and P polarized light.

On the other hand, the refractive indices for the S polarized light and P polarized light incident upon this substrate 12 as inclined by an angle $\theta i$ with respect to the optical axis (in the direction vertical to the substrate plane) indicated by the reference numeral 12a in FIG. 3 are determined as follows.

FIG. 3 is an explanatory view showing the relation between an incident angle $\theta i$ of the light incident upon the substrate 12 and the refractive index.

The injection-molded PC substrate shows a substantially uniaxial crystal characteristic and two of the main refractive indices $n_1$, $n_2$ and $n_3$ are equal to each other. If a refractive index ellipsoid is indicated by selecting the axes of coordinates so that $n_1 = n_2$ and the Z axis direction may be $n_3$, the optical axis 12a will coincide with Z axis.

Here, the refractive index n' for the S polarized light incident as inclined by the angle $\theta i$ with respect to the optical axis (the direction vertical to the substrate plane) 12a and the refractive index n" for the P polarized light are represented by the minor axis 26a and major axis 26b of the vertically sectioned area (ellipse 26) of the light 25' after the incidence. That is to say, if the angle formed by the light 25 after the incidence with the optical axis is $\theta t$, $$n' = n_1 \tag{1}$$

$$n'' = n_1 n_3 / \sqrt{n_1^2 \sin^2 \theta t + n_3^2 \cos^2 \theta t} \tag{2}$$

Here, $\sin \theta t = (1/n') \sin \theta i$

Therefore, the beam portion 21 of the S polarized light incident upon the substrate 12 and the beam portion 22 of the P polarized light hold linear polarized lights but, for example, as the beam portions 23 and 24 incident as inclined by 45 degrees with respect to the above mentioned beam portions 21 and 22 are polarized lights including both components of the S polarized light and P polarized light a phase difference will be produced between the S polarized light component and the P polarized light component and the linearly polarized light will become an elliptically polarized light. If the thickness of the substrate 12 is represented by d and the wave length is represented by $\lambda$, this phase difference will be represented by $$\delta_{s-p} = (2\pi/\lambda) \cdot (n' - n'') \cdot (d / \cos \theta t)$$

Therefore, the larger the thickness d of the substrate and the incident angle $\theta i$, the larger the phase difference $\delta_{s-p}$.

FIG. 4 is a cross-sectioned view of a beam incident upon the objective by a linear polarization of a polarized direction represented by the reference numeral 27, reflected by the disc 11 and then again passing through the objective. In the beam incident upon the substrate, the nearer to the peripheral edge side, that is, the larger the aperture, the larger the angle $\theta_1$ of incidence and the phase difference $\delta_{s-p}$. Where the orientation angle (the angle formed by the incident plane and polarizing direction) corresponds to 45 degrees (that is 45 and 135 degrees), that is, at the reference numerals 28a, 28b, 28c and 28d, The ellipticity will become maximum.

Thus, in case the substrate shows a double refraction, even if the double refraction is of a uniaxial characteristic, by the refractive index for the thickness direction, the linear polarized light will become an elliptic light having a polarized light component at right angles with the linear polarized light direction.

Therefore, for example, in the case of being used for a substrate of a photomagnetic disc, the polarized direction of a returning light, in case a linearly polarized light is radiated, will rotate by a minute angle in response to the magnetizing direction but, even if a light analyzer is set so as to pass only the rotated polarized light component, the light beam having passed through the substrate will be made elliptic and therefore the beams other than the inherent signal component will also pass through this light analyzer and will mix into the signal. Also, there will be produced a signal component intercepted by the analyzer due to the ellipticity. Thus, the C/N (carrier to noise ratio) will reduce.

The above mentioned ellipticity will be produced by the difference between n' and n". This refractive index n" derives from the the refractive index in the thickness direction.

Thus, in the case of being used for the substrate of a photomagnetic disc, the refractive index in the thickness direction will become a very important factor but its value can not be determined in the above mentioned prior art example.

Also, in the case of being used not only for the substrate of a photomagnetic disk but also for the substrate of a photodisc for the reproduction or the like of recorded information by the difference of the reflected light amount, there is extensively used an optical system wherein a light beam, made of circular polarized light from a linear polarized light having passed through a polarized beam splitter by using a $\lambda/4$ plate, is projected and this returning light is again made a linear polarized light in a polarized direction intersecting at right angles with the above mentioned linear polarized direction by the $\lambda/4$ and is efficiently branched to the information light detector side by the above mentioned beam splitter. However, in this case, too, due to the refractive index in the thickness direction of the substrate (having a value different from the refractive index in the substrate plane direction), the light will not be efficiently branched and the C/N (carrier to noise) reduced. Also, in case the lights are collected and projected, if the refractive index in the thickness direction of the substrate is different from the refractive index in the substrate plane, the light beam will not be sufficiently focused, the beam spot will become larger than in the case of the isotropic refractive index and therefore it will be unfavorable in the case of high density recording. In the case of the recording mode, the energy density will reduce, therefore the output of the light source will have to be made larger and high speed recording will be obstructed.

That is to say, in the case of not only a photomagnetic disc but also a photodisc, it is very important to know the value of the refractive index in the thickness direction of the substrate but, with the measuring apparatus of the above mentioned prior art example, the refractive index in the thickness direction can not be determined.

OBJECT AND SUMMARY OF THE INVENTION

An object of the present invention is to provide an apparatus for measuring the refractive index in the thickness direction of an optical recording medium substrate and a method of measuring the same.

In the refractive index measuring apparatus of the present invention, the incident angle of a polarized beam is set to be an oblique angle of incidence upon the substrate plane of an optical recording medium substrate. In this state, the polarized direction of the polarized beam is varied with respect to the substrate. The transmitted or reflected light beam by the substrate is received by a light receiving means through a light analyzing means in a crossed Nichol state. A received light amount for the polarization angle is measured and is compared with a theoretical formula so that the refractive index in the thickness direction of the substrate may be measured.

In the measuring method of the present invention, the angle incidence of a polarized beam upon the substrate plane is kept constant. The transmitted or reflected light amount by the substrate in the crossed Nichol state, in case the polarizing direction with respect to the substrate is varied, is measured. The refractive index in the thickness direction for the characteristic coinciding with the theoretical formula is determined and thereby the refractive index in the thickness direction of the substrate is determined.

BRIEF DESCRIPTION OF THE DRAWINGS

FIGS. 5 to 13 relate to the first embodiment of the present invention.

FIG. 5 is a formation view showing a refractive index measuring apparatus of the first embodiment.

FIG. 7 is a graph showing optical outputs actually measured with a light receiving means in case the polarized direction is varied.

FIG. 8 is an explanatory view showing the relation of the polarized plane before and after refraction when a light beam is incident.

FIG. 9 is a graph showing the relation between the polarized direction and optical output when an angle Φ, representing the direction of the optical axis from the theoretical formula, is made a parameter.

FIG. 10 is a graph showing the relation between the polarized direction determined from the theoretical formula and the optical output when the refractive index ne in the thickness direction is made a parameter.

FIG. 11 is a graph showing the optical output for the polarized direction in the case that the angle Φ representing the optical axis from the theoretical formula is varied under 0°.

FIG. 12 is a graph showing the relation between the polarized direction at a refractive index ne different from that in FIG. 7 from the theoretical formula and the optical output.

DETAILED DESCRIPTION OF PREFERRED EMBODIMENTS

The present invention shall be concretely explained in the following with reference to the drawings.

Figure 5:
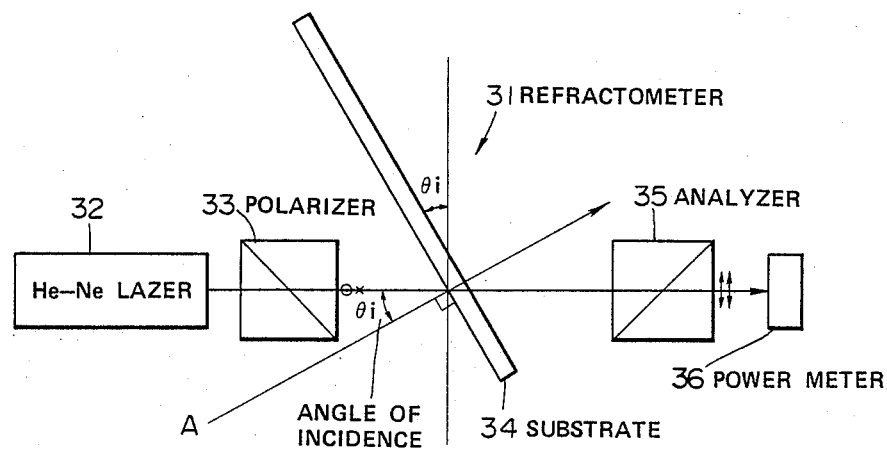

As shown in FIG. 5, in a refractive index measuring apparatus 31 of the first embodiment, a random polarized laser beam, generated by an He-Ne laser 32 as a light source, is passed through a polarizer 33 such as a GTP so as to be linearly polarized. Then this linear polarized beam is incident upon a substrate 34 arranged as inclined so that the angle formed by this beam and a line vertical to the surface, that is, the angle $\theta_1$ of incidence, may be a proper angle. The beam passing through this substrate 34 is received by a powermeter 36 as a light receiving means through a light analyzer 35 such as a GTP to determine the light receiving output. The above mentioned angle $\theta_1$ of incidence can be set by varying the supporting angle of a supporting means on the optical system side or substrate 34 side.

In this measuring example, the substrate 34, in which the refractive index in the thickness direction is measured, is injection molded, for example, of a PC resin so as to be in the form of a disc the same as in the actual disc-shaped recording medium substrate and is, for example, of a diameter of 120 mm and thickness of 1.2 mm.

The plane of incidence upon and through which the above mentioned polarized beam is to be incident and refracted and to be passed is so set as to pass through the center 0 of the disc substrate 34.

Figure 1:
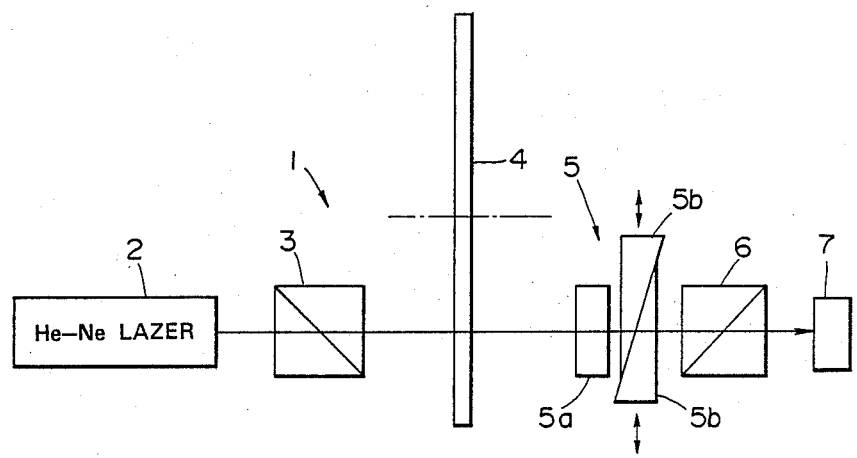
FIG. 1 is a formation view showing a prior art example.

Now, by using the apparatus which is a prior art example of FIG. 1 the above mentioned PC substrate 34 shows substantially no anisotropy in the substrate plane. That is to say, $n_1 \simeq n_2$ (expressed substantially as $n_1 = n_2$) among the main refractive indices $n_1$, $n_2$ and $n_3$. Also, in the case of injection-molding this substrate, these rectractive indices will be in the substrate plane (substantially, one of the refractive indices $n_1$ and $n_2$ will coincide with that in the radial direction of the disk and the other will be in the direction intersecting at right angles with this radial direction) and the refractive index in the thickness direction will substantially coincide with $n_3$. The method of measuring this refractive index $n_3$ in the thickness direction by using the measuring apparatus 31 shown in FIG. 5 shall be explained in the following.

In this measuring method, the above mentioned angle $\theta i$ of incidence is kept constant and the polarized direction of the incident light beam incident upon the substrate 34 is varied to determine the output I of the powermeter 36 for the varied angle in the polarized direction. In the case, it is necessary to set a reference angle to be an angle of 0° in the polarized direction. However, this reference angle is so set that, for example, the polarized direction may intersect at right angles with the plane of incidence including the radial direction of the substrate 34 and may be parallel with the substrate surface, that is it may be as shown in FIG. 5 or FIGS. 6(a)-6(d) as seen from the direction indicated by the arrow A in FIG. 5. The polarized direction incident upon the substrate 34 is varied by rotating the polarizer 33 from this state and the angle formed by the polarized direction in this case and the (tangential) direction (in FIG. 6(a), this straight line is indicated by the reference symbols ls and is parallel with the polarized direction indicated by the arrow B) intersecting at right angles with the radial direction in the substrate plane is defined as a polarization angle Ψ'.

The polarized direction of the polarized beam incident upon the above mentioned substrate is set by rotating the polarizer 33 and, with the rotation of this polarizer 33, the light analyzer will be also rotated and both will be held in the crossed Nichol state.

Figure 6A:
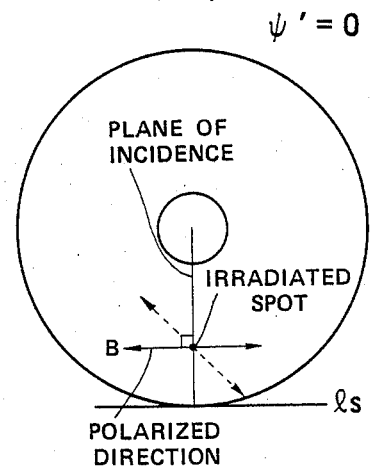
FIGS. 6(a)–6(d) are an explanatory view showing respective polarized directions in a beam spot position on the substrate.
Figure 6B:
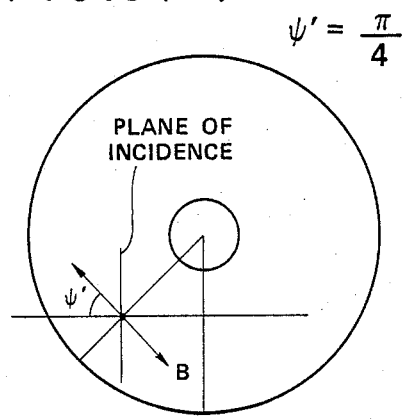
Figure 6C:
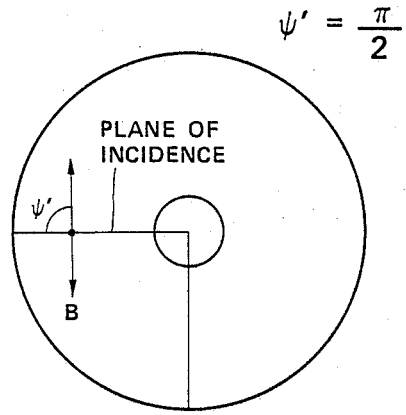
Figure 6D:
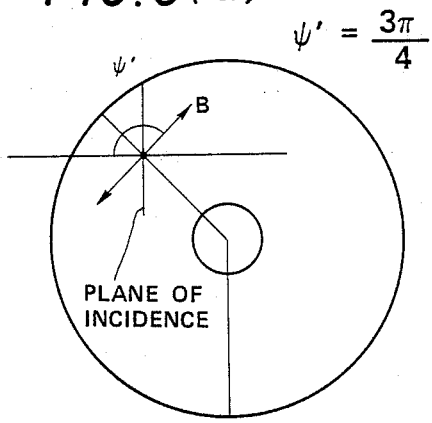

In the case of the above mentioned FIG. 6(a), the incident light will be only the S polarized light component. In case the polarized direction is varied, for example, by $\pi/4$ from the state in the above mentioned FIG. 6(a), polarized direction such as is shown by the dotted line in FIG. 6(a) will be made. If this state is indicated by rotating the substrate 34 side, it will be as shown in FIG. 6(b). Here, the angle Ψ' will be $\pi/4$ and will have the S polarized light and P polarized light components. When the polarizer 33 is further rotated so that the rotation angle may be made $\pi/2$ from the state in FIG. 6(a), the state shown in FIG. 6(c) will be made and, when the rotation angle is made $3\pi/4$, the state shown in FIG. 6(d) will be made.

Figure 7:
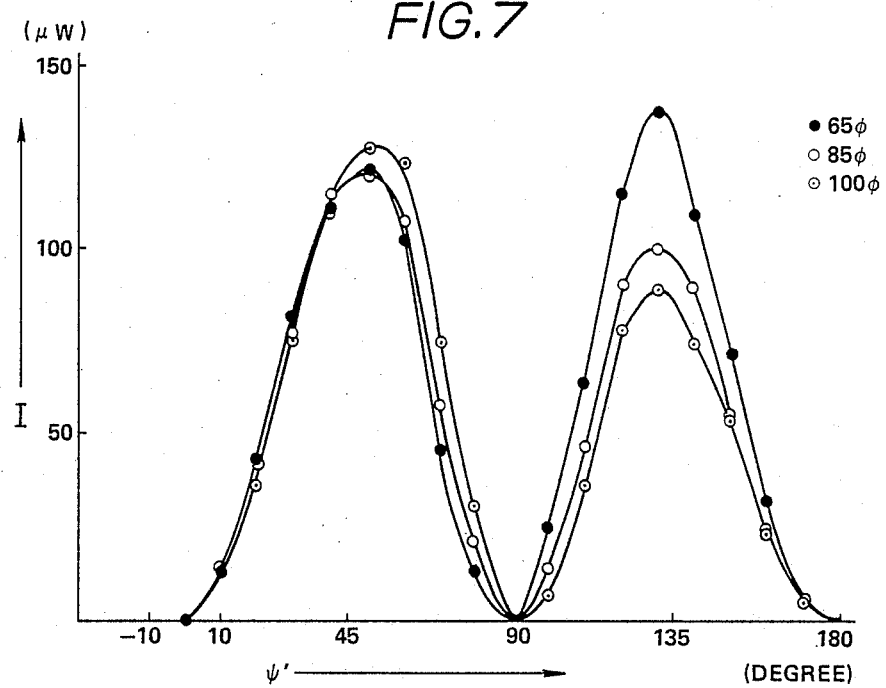

In case the polarized direction of the above mentioned polarized beam is varied little by little, the light receiving amount output of the beam passing through the substrate will be as shown in FIG. 7. In this embodiment, the angle $\theta i$ of incidence is set at 30° and the maximum of the light passing through the substrate is made mW. The measured values in FIG. 7 show the results measured in the respective positions of 65Φ, 85Φ and 100Φ on the substrate. The cause of producing some differences depending on the above mentioned respective irradiating positions shall be described later but it is thought to be because the injection-molded state is somewhat different in the respective positions of the substrate 34 and therefore the optical axis direction is also somewhat different.

It is found from this FIG. 7 that, in case the angle Ψ' is made 0° and 90°, that is, corresponds to the S polarized light or P polarized light, the output I=0 will be obtained and no ellipse will be made. At other angles, that is, in case the P polarized light and S polarized light are mixed together, the ellipticity will occur and will become maximum at 45° and 135° as described above.

It is anticipated that the larger the difference between the respective indices for the S polarized light and P polarized light, the more conspicuous the ellipticity. The refractive index in the thickness direction can be known from the theoretical fomula in case the measured value is compared and best coincides with the theoretical formula.

The theoretical formula for determining the refractive index shall be explained in the following.

Figure 8:
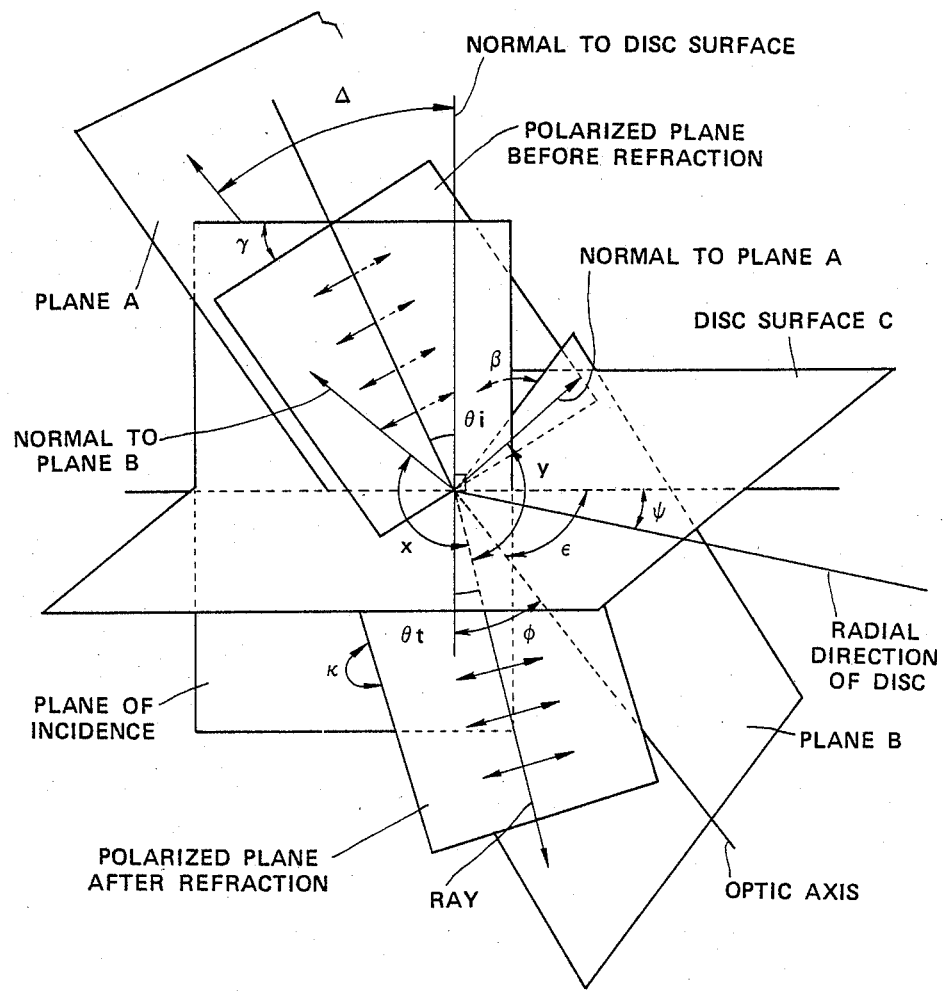

FIG. 8 is an explanatory view showing the variation of the polarized plane in the case a light beam is incident upon a medium. The plane A is a plane including the optical axis and vertical to the plane of incidence and the plane B is a plane including the light after the refraction and the optical axis.

After the refraction of the light beam incident upon a medium, the angle formed by the polarized plane and optical axis as seen from the light direction is represented by $\theta$, the angle of incidence is represented by $\theta i$, and the angle formed by the plane of incidence and the radial direction is represented Ψ.

Figure 2:
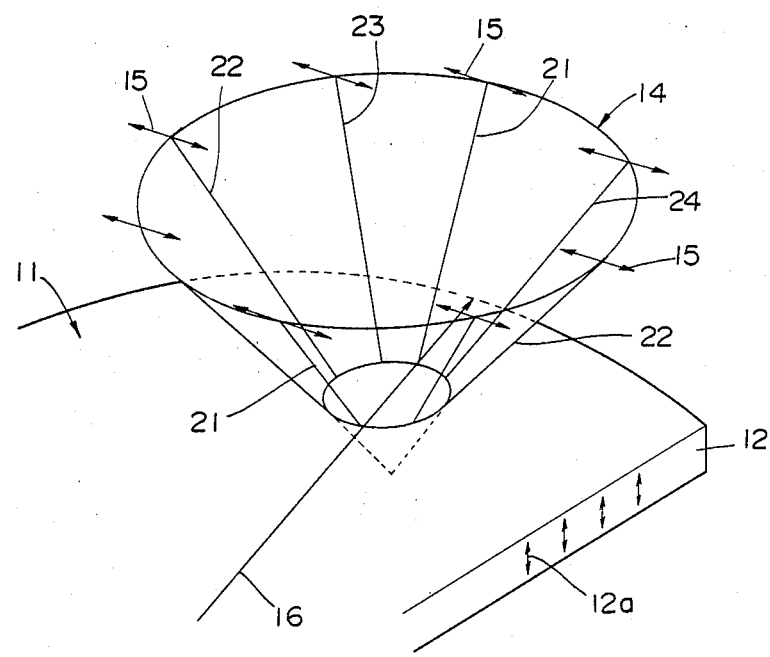
FIG. 2 is an explanatory view showing the manner of beams in case light beams are collected on a substrate.
Figure 3:
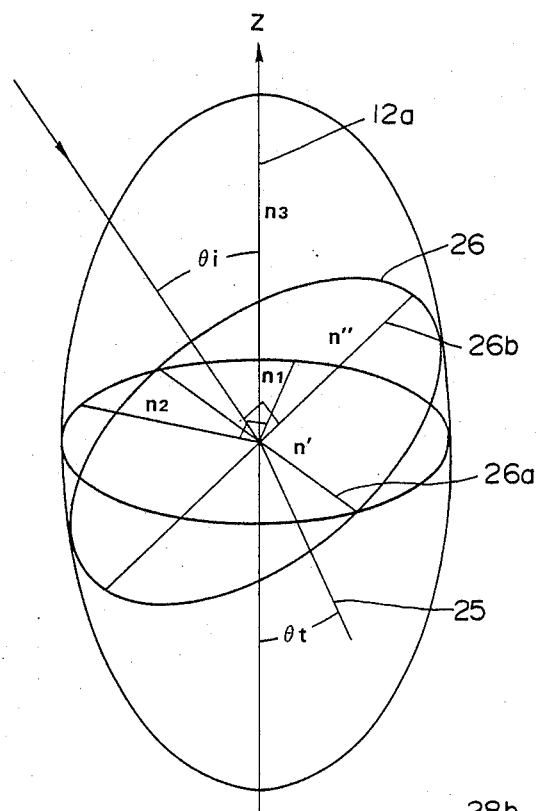
FIG. 3 is an explanatory view showing the relation between the angle of incidence of the light incident upon the substrate and the refractive index.
Figure 4:
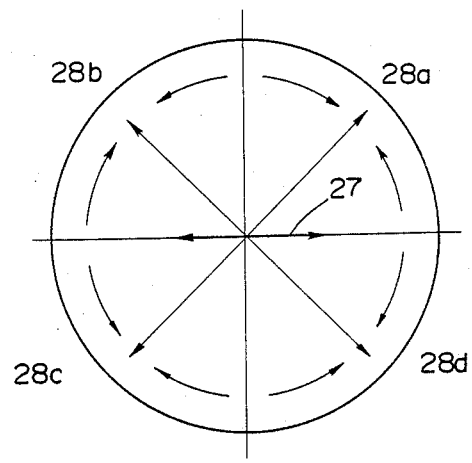
FIG. 4 is an explanatory view showing the relation between the position on the cross-section of a beam reflected by the disc and then passing through an objective and the degree of the elliptic polarization.

This angle Ψ is defined as an angle formed by the incident beam position in the light beam 14 in FIG. 2 with the radial direction. That is to say, in FIG. 2, in the case of the reference numeral 21, Ψ=0 and the angle Ψ will be substantially identical with the above mentioned angle Ψ'.

Further, the other angles are respectively defined as follows:

$\epsilon$: the angle between the optical axis and the plane of incidence.

$\gamma$: the angle between the polarized plane and the plane of incidence before the refraction as seen from the light direction.

$\kappa$: the angle between the polarized plane and the plane of incidence as seen from the light direction after the refraction.

$\beta$: the angle between the optical axis and the plane of incidence as seen from the light direction after the refraction.

$\theta t$: the angle formed by the light with the boundary normal after the refraction.

In the above, $$\theta t = \beta + \kappa \quad (4)$$

On the other hand, $\kappa$ is obtained from $\gamma$, $\theta i$, $\theta t$, and Fresnel's Formula as follows $$\tan\kappa = \cos(\theta i - \theta t) \cdot \tan\gamma$$

hence $$\kappa = \tan^{-1}\{\cos(\theta i - \theta t) \cdot \tan\gamma\} \quad (5)$$

If the optical axis is inclined in the plane vertical to the boundary surface including the radial direction with respect to the boundary surface by an angle of certain degrees and the angle formed by the normal to the boundary surface and the optical axis in the radial direction is represented by Φ, the relation between Φ, Ψ, and $\epsilon$ will be given by $$\sin\epsilon = \sin\Phi \cdot \sin\psi \quad (6)$$

Where, if the angle formed by the plane (the plane A in FIG. 8) including the optical axis and vertical to the plane of incidence and the normal to the boundary surface is represented by Δ, the relation between Δ, $\epsilon$, and Ψ will be given by $$\sin\Delta = \frac{\tan\epsilon}{\tan\Psi} \quad (7)$$

Further, if the angle formed by the normal (in the plane of incidence) to the plane including the optical axis and vertical to the plane of incidence and the light direction after the refraction is represented by $\gamma$, then the relation between $\beta$, $\epsilon$, and $\gamma$ will be given by $$\tan\beta = \tan\epsilon \cdot \frac{1}{\cos y}$$

that is, from $$y = \left\{ \frac{\pi}{2} - (\theta_t + \Delta) \right\}$$

$$\tan\beta = \tan\epsilon \cdot \frac{1}{\sin(\theta_t + \Delta)} \quad (8)$$

from the formulae (7) and (8)

$$\tan\beta = \frac{\sin\Psi \cdot \sin\Phi}{\sin\theta_t \cdot \cos\Phi + \cos\theta_t \cdot \cos\Psi \cdot \sin\Phi} \quad (9)$$

will obtained.

Assuming that the polarized plane before being converged is vertical to the radial direction $$\tan\gamma = \frac{\tan\left(\frac{\pi}{2} - \Psi\right)}{\cos\theta_1}. \quad (10)$$

therefore from the formulae (5), (6), (10) and (11), $\theta$ is obtained as follows.

$$\theta = \tan^{-1}\left( \frac{\sin\Psi \cdot \sin\Phi}{\sin\theta_t \cdot \cos\Phi + \cos\theta_t \cdot \cos\Psi \cdot \sin\Phi} \right) + \tan^{-1}\left\{ \frac{\cos(\theta_1 - \theta_t)}{\tan\Psi \cdot \cos\theta_1} \right\} \quad (11)$$

where $$\theta_t = \sin^{-1}\left( \frac{\sin\theta_1}{n} \right)$$

Here, the phase difference $\alpha$ is expressed by $\theta i$ and $\Psi$. Generally $$\alpha = \frac{2\pi}{\lambda}(n'' - n')h \quad (12)$$

where n' and n'' represent two refractive indices in the directions vertical to each other h represents a thickness
$\lambda$ represents a wave length.

If a uniaxial crystal is considered, $$n' = n_0 \quad (13)$$

On the other hand, when a refractive index ellipsoid is assumed for n'' and the angle formed by the optical axis and the light direction after the refraction is represented by x, $$n'' = \frac{n_e \cdot n_0}{\sqrt{n_0^2 + (n_e^2 - n_0^2)\sin X}} \quad (14)$$

where $$\sin x = \cos\theta t \cdot \cos\Phi - \cos\Psi \cdot \sin\theta t \cdot \sin\Phi \quad (15)$$

From the formulae (14) and (15), $$n'' = \frac{n_e \cdot n_0}{\sqrt{n_0^2 + (n_e^2 - n_0^2)\cos\theta t \cdot \cos\Phi - \cos\Psi \cdot \sin\theta t \cdot \sin\Phi)^2}} \quad (16)$$

Therefore from the formulae (12), (13) and (14), the phase difference $\alpha$ is obtained as follows.

$$\alpha = (2\pi/\lambda) \cdot \left( \frac{n_e}{\sqrt{n_0^2 + (n_e^2 - n_0^2)(\cos\theta t \cdot \cos\Phi - \cos\Psi \cdot \sin\theta t \cdot \sin\Phi)^2}} - 1 \right) n_0 \cdot h \quad (17)$$

That is to say, in case the optical axis is inclined by an angle of certain degrees with respect to the boundary surface in the plane vertical to the boundary surface including the radial direction, if a linear polarized light having a vibrating plane parallel with the radial direction is incident upon the boundary surface at a certain angle, the transmitted light will be seen to become elliptic. And the ratio of its minor axis to major axis will be given by $$\frac{\text{minor axis}}{\text{major maxis}} = \sqrt{I_s} = \frac{|\sin 2\theta \cdot \sin\alpha|}{1 + \sqrt{1 - \sin^2 2\theta \cdot \sin 2\alpha}} \quad (18)$$

On the other hand, $\theta$ and $\alpha$ are represented by the formulae (11) and (16), respectively, and both $\theta$ and $\alpha$ are the functions of $\theta i$, $\Psi$ and $\Phi$. Therefore once the values of $\theta i$, $\Psi$, $\Phi$, $n_0$, and $n_e$ are determined, the degree of becoming elliptic, that is the ratio of the minor axis to major axes can be obtained.

Here, in order to enable the comparison with the experimental results, if the formula (17) is converted and the light intensity I in the direction of the minor axis is determined, $$I = I_0 \cdot T \frac{(\text{minor axis})^2}{(\text{major maxis})^2 (\text{minor axis})^2} = I_0 \cdot T \frac{I_s}{I + I_s} \quad (19)$$

where, $I_0$ is the intensity of the incident light an T is the transmittance.

Figure 9:
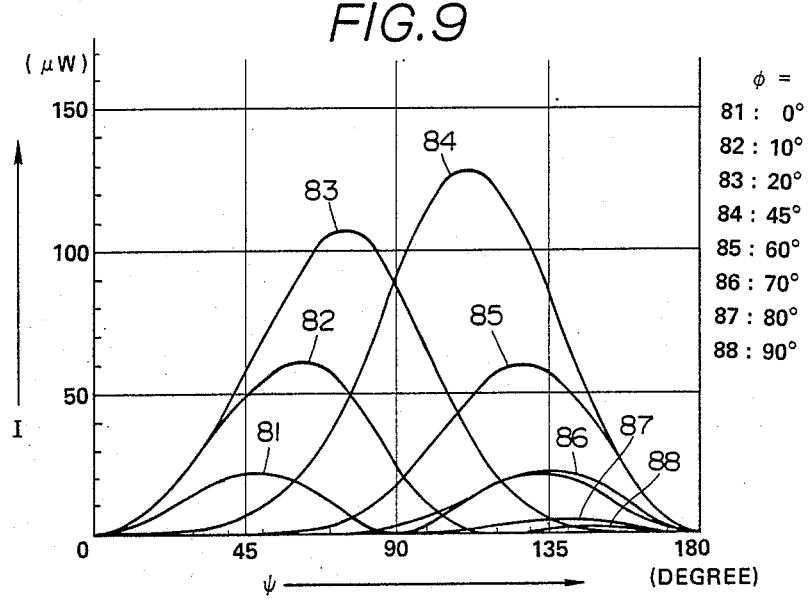

To make the conditions coincide with the experiments, if $I_0 \cdot T = 1$ mW, then $$I = \frac{I_s}{I + I_s} \quad (20)$$

will be obtained,

FIG. 9 is a graph showing the calculated results of the relationship between I and $\Psi(=\Psi')$ when $\Phi$ is varied as determined from the above mentioned theoretical formulas (11), (16), (17), and (19).

At this time, the values of $\theta i$, $n_0$, and $n_e$ are set as $\theta i = 30°$, $n_0 = 1.58000$, and $n_e = 1.58025$.

The values of n and $\Phi$ can be determined from the ordinry refractive index measurement and are made to coincide with those of the PC substrate 34.

The case that Φ is varied from 0° (81 in the graph) to 90° (88 in the graph) is shown in the graph. It is seen from the graph that the case in which Φ=0°, that is, the behavior marked by 81 in the graph is close to the actually measured results by the PC substrate.

Figure 10:
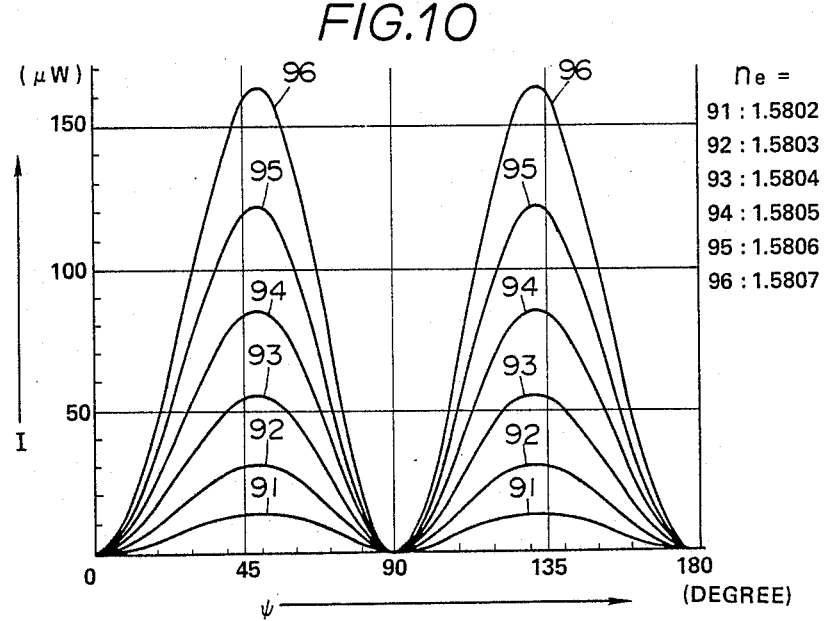

On the other hand, FIG. 10 is a graph showing the results obtained from the theoretical formulae the same as in the case of FIG. 9 of the relationship between I and Ψ when ne is varied. That is, there is shown the case that $\theta i=30°$, $n_0=1.58000$, Φ=0° and ne is varied from 1.5802 (91 in the graph), to 1.5807 (96 in the graph). From this graph, it is seen to be possible to substantially reproduce the actual measuring conditions by the PC substrate shown in FIG. 7 by selecting adequate values of ne.

Now, in the measured values shown in the above mentioned FIG. 7, the peak values of the angle Φ of 45° and 135° are somewhat different because the optical axis in the irradiated spot position in the substrate is a little displaced from the direction vertical to the substrate plane. That is to say, by calculating in detail the periphery of Φ=0° in FIG. 9, some difference when the angle Ψ' is 45° and 135° as in the actually measured values can be derived.

Figure 11:
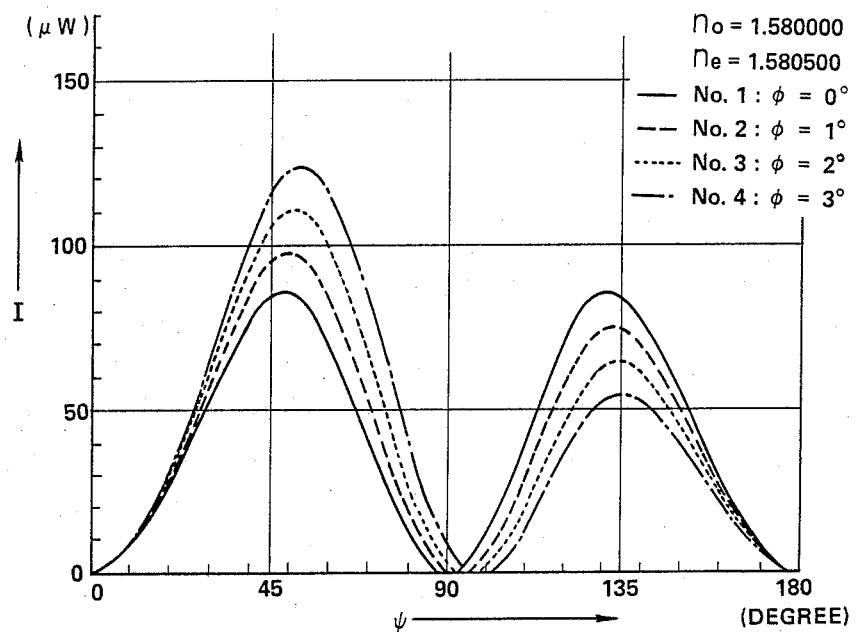
Figure 12:
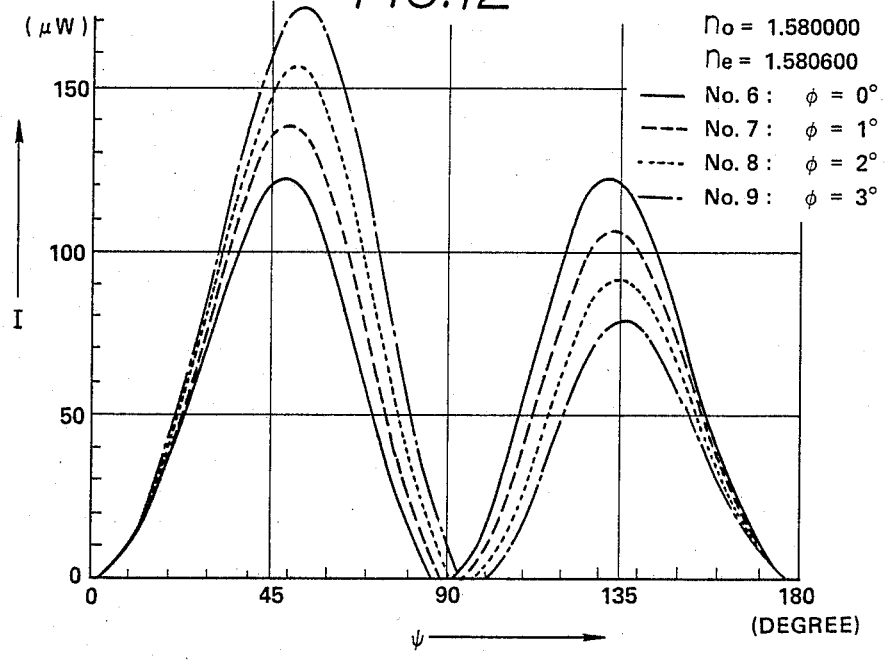

FIGS. 11 and 12 show the output I for the angle Φ' in case the angle Φ in the case that $n_1=n_2=n_0=1.580000$ and the refractive index $n_3(=ne)$ in the thickness direction is varied to be respectively 1.580500 and 1.580600 is varied to be 0°, 1°, 2° and 3°. The angle of incidence $\theta i$ is made 30° in any case.

By determining the parameter values (Φ and ne) of the best coinciding graph by comparing the measured graph of FIG. 7 with the theoretical graphs of FIGS. 9 to 12, it is found that, in the PC substrate 34 used in the above mentioned measurement, the optical axis is substantially vertical (Φ=0 to 2°) to the substrate plane and the refractive index ne in the thickness direction is 1.5806.

Figure 13A:
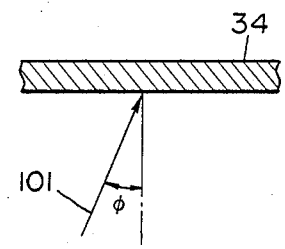
FIGS. 13(a)–13(b) are an explanatory view showing the measured direction of the optical axis of a PC substrate.
Figure 13B:
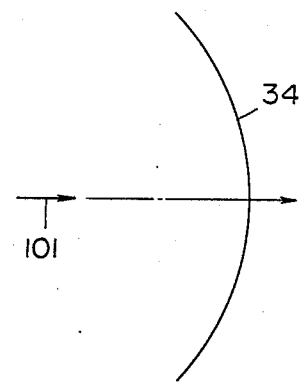

The above results shall be explained with reference to FIGS. 13(a) and 13(b). That is to say, it is found that, in the PC substrate 34, the optical axis 101 is in a plane vertical to the substrate surface including the radial direction and the angle Φ formed by the normal to the substrate surface and the optical axis is near 0 degree. FIG. 13(a) is an explanatory view as seen from the cross-sectional direction of the substrate and FIG. 13(b) is an explanatory view as seen from the direction vertical to the substrate surface.

Thus, according to the first embodiment, by determining a graph as in FIG. 7 in which the received light amounts of the light receiving means in the respective polarized directions are measured by keeping the angle $\theta i$ of incidence constant and varying the polarized direction (that is, the angle Φ') and, on the other hand, by comparing it with the graph of the received light amounts for the polarized directions in the case that the respective parameters in the theoretical formulae are varied, the respective parameter values in the graph best coinciding with the measured graph are determined and thus the refractive index in the thickness direction can be easily determined with the apparatus of a simple formation shown in FIG. 5.

In case the substrate 34, used for the recording medium, is substantially optically equal in all the radial directions, by rotating the substrate around its center axis in FIG. 5, the output I of the powermeter 36 will not vary. However, in the PC substrate showing uniaxial characteristic, if the optical axis is nearly vertical to the substrate plane but is displaced or the like from the vertical direction in some place, the output I will vary. Therefore, in the measuring apparatus 31 shown in FIG. 5, by rotating the substrate 34, the uniformity of the optical characteristic in the peripheral direction of the plastic substrate can be checked by whether the output I in such case varies or not. Also, as shown in FIG. 7, by varying the measuring position in the radial direction, the uniformity of the optical characteristic in the radial direction can be checked.

Figure 14:
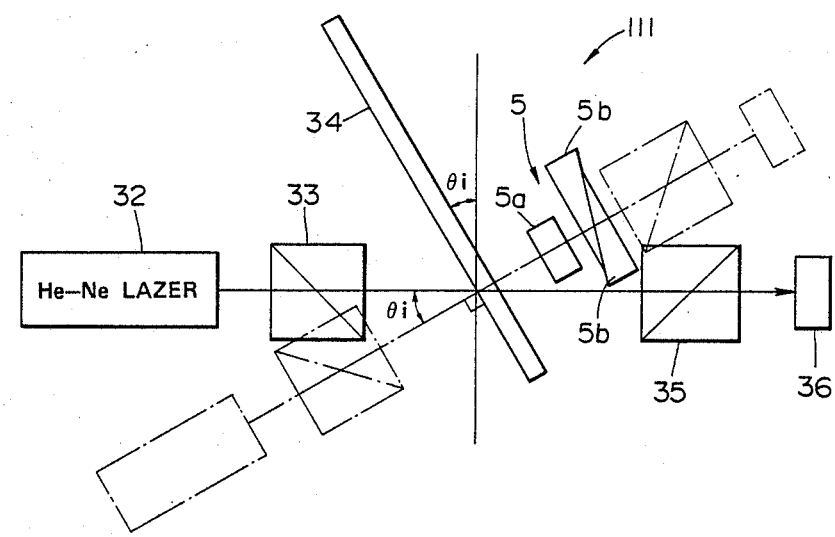
FIG. 14 is a formation view showing a measuring apparatus of the second embodiment of the present invention.

FIG. 14 shows an apparatus 111 for measuring the refractive index in the thickness direction of the second embodiment of the present invention.

In this measuring apparatus 111 of the second embodiment, in addition to the above mentioned apparatus 31 of the first embodiment, the phase compensating plate 5 of Babinet-soleil shown in FIG. 1 is arranged in the normal direction on the light transmitting side of the substrate 34 in the position in which the polarized beam is radiated by this apparatus 31. The He-Ne laser 32, polarizer 33, light analyzer 35 and powermeter 36 can be rotated and moved to the position indicated by the one-point chain line from the position indicated by the solid line. This rotation can be made at a high precision by using such holding means rotatable in the position of projecting polarized beams onto the substrate 34 as, for example, a goniometer.

In this measuring apparatus 111, the anisotropy of the refractive index in the substrate plane in the substrate 34 (not limited to the PC substrate) can be checked prior to determining, for example, the refractive index $n_3$ in the thickness direction.

That is to say, by rotating and moving the He-Ne laser, polarizer 33, light analyzer 35 and powermeter 36 to the position indicated by the one-point chain line, the refractive index measuring apparatus shown in FIG. 1 can be realized. On the other hand, when the light beam passing through this polarizer 33 and the light analyzer 35 held in the crossed Nichol state is received by the powermeter 36 and the phase compensating plate 5 is adjusted so that the output I of this powermeter 36 may be minimum, the refractive index anisotropy can be measured. The graph of the output I for the angle Ψ' influenced by the refractive index $n_3$ in the thickness direction is determined by setting the He-Ne laser 32 and the like in the position indicated by the solid line. From the graph of the measured values of the refractive index in the above mentioned substrate plane and the output I for the angle Ψ, in case a biaxial characteristic is shown, in case even a uniaxial chracteristic is not equal in all the radial directions and in case the optical axis is displaced from the direction vertical to the substrate plane, the refractive index in the thickness direction can be accurately determined. Thus, in case the characteristic is not uniform in all the radial directions, by making the plane of incidence coincide with the direction including the main refractive index, the refractive index in the thickness direction may be determined.

Figure 15:
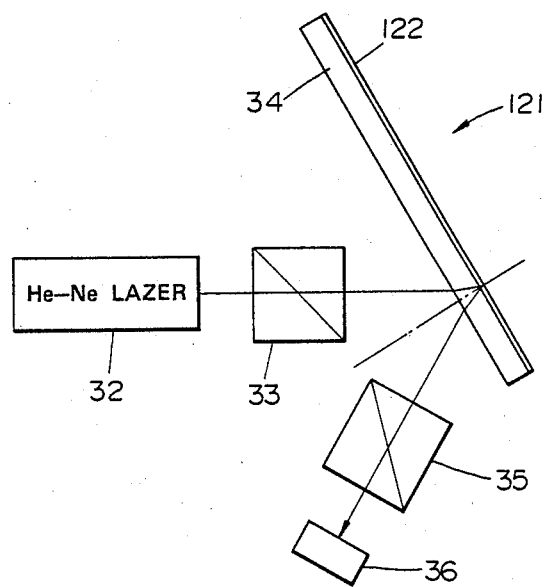
FIG. 15 is a formation view showing the third embodiment of the present invention.

In the above mentioned respective embodiments, the light passing through the substrate is received by the light receiving means but the present invention is not limited to it. For example, as shown in FIG. 15 the refractive index in the thickness direction may be measured by receiving the reflected light.

That is to say, in this measuring apparatus 121, the polarizer 36 and powermeter 36 are arranged on the side on which the light beam refracted by the substrate 34 and reflected by the reflecting film 122 on the back side becomes a mirror image with the incidence side with respect to the normal in the emitted direction, that is, in the incidence plane of the reflecting film 122.

In this case, the thickness d of the substrate 34 will be substantially twice as large in the operation.

In the above described respective embodiments, the form of the substrate in which the refractive index in the thickness direction is measured is explained to be disk-shaped but the measuring apparatus or measuring method of the present invention is not limited to it and the form may be flat plate-shaped.

Also, in the above mentioned respective embodiments, the He-Ne laser generating random polarized laser lights with a substantially single wave length is used as a light source but the present invention is not limited to it. For example, a semiconductor laser may be used. In such case, polarized light beams will be generated and therefore the polarizer and the like may be omitted. The polarized direction may be varied not only by rotating the polarizer or the like but also by rotating the substrate side around the projected beam spot position as a center.

What is claimed is:

1. An apparatus for measuring a refractive index of a substrate for an optical recording medium comprising:
    a light source generating a light beam of a substantially single wavelength;
    a polarizing means linearly polarizing said light beam;
    an angle setting means for setting an oblique angle of incidence, wherein said linearly polarized light beam, having passed through said polarizing means, is incident at the oblique angle of incidence upon a flat plate-shaped plane of said substrate for an optical recording medium to have the refractive index measured;
    a light analyzing means arranged on at least one of a transmitted light side and a reflected light side of said substrate and held in a crossed Nichol state with said polarizing means;
    a light receiving means receiving said light beam having passed through said light analyzing means;
    a varying means for relatively varying the direction of said linear polarized light with said angle of incidence kept constant while maintaining the crossed Nichol state between said light analyzing means and said polarizing means; and
    comparing means for comparing an output of the light receiving means for the varied angle in the polarized direction with a theoretical formula in order to determine the refractive index of said substrate.

2. A measuring apparatus according to claim 1 wherein said light source and polarizing means are formed of semiconductor lasers generating polarized light beams.

3. A measuring apparatus according to claim 1 wherein said varying means is so formed as to rotate the substrate side around a projected beam spot position as a center.

4. A measuring apparatus according to claim 1 wherein a Babinet-Soleil phase compensating plate is arranged in a normal direction of the transmitting light side of the substrate so as to be able to eliminate an anisotropy of the refractive index in the substrate plane.

5. A method of measuring the refractive index of a substrate for an optical recording medium comprising of the steps of:
    linearly polarizing a light beam of a substantially single wavelength;
    incidenting said linear polarized light beam at an oblique angle to incidence upon a flat plate-shaped substrate plane to have the refractive index in the thickness direction measured;
    varying a direction of said linearly polarized light with respect to said substrate in said plane of incidence;
    passing transmitted or reflected light beam by said substrate through a light analyzing means in a crossed Nichol state with the direction of said linear polarized light to determine the optical output characteristic of a light receiving means; and
    measuring the refractive index in the thickness direction of the substrate by comparing the optical output of the light receiving means with a theoretical formula.

* * * * *